United States Patent
Iwamoto et al.

(10) Patent No.: US 11,377,406 B2
(45) Date of Patent: *Jul. 5, 2022

(54) FLUOROETHANE PRODUCTION METHOD AND FLUOROOLEFIN PRODUCTION METHOD

(71) Applicant: DAIKIN INDUSTRIES, LTD., Osaka (JP)

(72) Inventors: Tomoyuki Iwamoto, Osaka (JP); Takashi Usui, Osaka (JP); Takehiro Chaki, Osaka (JP); Kazuhiro Takahashi, Osaka (JP); Tsubasa Nakaue, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/350,785

(22) Filed: Jun. 17, 2021

(65) Prior Publication Data
US 2021/0309593 A1    Oct. 7, 2021

Related U.S. Application Data

(63) Continuation of application No. PCT/JP2019/049608, filed on Dec. 18, 2019.

(30) Foreign Application Priority Data

Dec. 19, 2018   (JP) .............................. JP2018-237661

(51) Int. Cl.
*C07C 17/087*    (2006.01)
*B01J 19/24*     (2006.01)
(Continued)

(52) U.S. Cl.
CPC ........... *C07C 17/087* (2013.01); *B01J 19/242* (2013.01); *B01J 21/18* (2013.01); *B01J 23/44* (2013.01);
(Continued)

(58) Field of Classification Search
CPC ....... C07C 17/087; C07C 17/25; C07C 17/35; C07C 17/354; C07C 19/18; C07C 21/18; B01J 23/44
See application file for complete search history.

(56) References Cited

U.S. PATENT DOCUMENTS 3,432,562 A    3/1969   Gardner
5,059,729 A   10/1991   Gervasutti
(Continued)

FOREIGN PATENT DOCUMENTS

EP    0 234 002    9/1987
EP    3 792 237    3/2021
(Continued)

OTHER PUBLICATIONS

International Search Report dated Mar. 10, 2020 in International (PCT) Application No. PCT/JP2019/049608.
(Continued)

*Primary Examiner* — Jafar F Parsa
(74) *Attorney, Agent, or Firm* — Wenderoth, Lind & Ponack, L.L.P.

(57) ABSTRACT

The production method according to the present disclosure comprises obtaining a product comprising a fluoroethane from a fluoroethylene by a reaction in the presence of at least one catalyst. The reaction is performed in two or more reaction zones. Each reaction zone comprises a catalyst, and the fluoroethylene is supplied to each reaction zone to perform the reaction.

7 Claims, 1 Drawing Sheet

(51) Int. Cl.
　　　*B01J 21/18*　　　(2006.01)
　　　*B01J 23/44*　　　(2006.01)
　　　*C07C 17/25*　　　(2006.01)
(52) U.S. Cl.
　　　CPC ..... *C07C 17/25* (2013.01); *B01J 2219/00087*
　　　　　(2013.01); *B01J 2219/00164* (2013.01)

(56) References Cited

U.S. PATENT DOCUMENTS

| | | | |
|---|---|---|---|
| 5,626,790 | A | 5/1997 | Minor |
| 2011/0071325 | A1 | 3/2011 | Ohno et al. |
| 2013/0006022 | A1 | 1/2013 | Shiotani et al. |
| 2016/0168059 | A1* | 6/2016 | Shiotani ............ C07C 17/23 570/175 |
| 2017/0327442 | A1* | 11/2017 | Wendlinger ........ C07C 17/25 |

FOREIGN PATENT DOCUMENTS

| | | |
|---|---|---|
| GB | 2 311 522 | 10/1997 |
| JP | 62-169737 | 7/1987 |
| JP | 1-287044 | 11/1989 |
| JP | 9-255598 | 9/1997 |
| JP | 2010-533151 | 10/2010 |
| JP | 2014-510027 | 4/2014 |
| JP | 2017-537131 | 12/2017 |
| WO | 2009/010472 | 1/2009 |
| WO | 2009/139352 | 11/2009 |
| WO | 2011/122157 | 10/2011 |
| WO | 2012/094477 | 7/2012 |
| WO | 2016/092340 | 6/2016 |
| WO | 2017/104828 | 6/2017 |
| WO | 2019/216175 | 11/2019 |

OTHER PUBLICATIONS

International Search Report dated Mar. 10, 2020 in International (PCT) Application No. PCT/JP2019/049595.
Sigma "Trifluoroethylene" Deposited and Available date Mar. 3, 2017 (Year: 2017).
International Search Report dated Apr. 14, 2020 in International (PCT) Application No. PCT/JP2020/002548.

* cited by examiner

FLUOROETHANE PRODUCTION METHOD AND FLUOROOLEFIN PRODUCTION METHOD

TECHNICAL FIELD

The present disclosure relates to a method for producing a fluoroethane, and a method for producing a fluoroolefin.

BACKGROUND ART

Fluoroethanes typified by 1,1,2-trifluoroethane (hereinafter referred to as "HFC-143") are known as a starting material for producing various refrigerants. Various methods have been proposed for the production of fluoroethanes such as HFC-143.

For example, Patent Literature 1 proposes a technique for producing HFC-143 by a hydrogenation reaction of chlorotrifluoroethylene or the like, in the presence of a hydrogenation catalyst.

CITATION LIST

Patent Literature

PTL 1: JPH1-287044A

SUMMARY

For example, the present disclosure includes the inventions described in the following items.
Item 1
A method for producing a fluoroethane represented by the following formula (1):
$CX^1X^2FCX^3X^4X^5$ (1), wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom,
the method comprising obtaining a product comprising the fluoroethane from a fluoroethylene represented by the following formula (3) by a reaction in the presence of at least one catalyst:
$CX^9F=CX^{10}X^{11}$ (3), wherein $X^9$, $X^{10}$, and $X^{11}$ are the same or different and each represents a hydrogen atom, a fluorine atom, or a chlorine atom,
wherein the reaction is performed in two or more reaction zones, and each reaction zone comprises a catalyst; and
the fluoroethylene is supplied to each reaction zone to perform the reaction.

Advantageous Effects of Invention

The production method according to the present disclosure enables the desired fluoroethane to be obtained with high selectivity.

DESCRIPTION OF EMBODIMENTS

The present inventors found that in the production of a fluoroethane, when a fluoroethane such as HFC-143 (1,1,2-trifluoroethane) is produced according to, for example, the method disclosed in Patent Literature 1, the selectivity of the desired fluoroethane is poor in many cases.

The inventors also confirmed that the method disclosed in Patent Literature 1 causes significant blockage and corrosion of the reactor during the reaction. In particular, when the capacity of the reactor is increased (i.e., when the reactor is scaled up for mass production), the selectivity decreases more notably, and blockage and corrosion of the reactor occur during the reaction.

The inventors conducted extensive research to achieve the object of providing a production method that enables the desired fluoroethane to be obtained with high selectivity, and that is less likely to cause blockage and corrosion of a reactor. The inventors consequently found that the above object can be achieved by performing a reaction in two or more reaction zones, providing each reaction zone with a catalyst, and supplying a fluoroethylene to each reaction zone to perform the reaction.

Embodiments included in the present disclosure are described in detail below. In the present specification, the tams "comprise" and "contain" include the concepts of "comprise," "contain," "consist essentially of," and "consist of."

1. Method for Producing Fluoroethane

In the production method according to the present disclosure, a fluoroethane represented by the following formula (1) is produced:

$$CX^1X^2FCX^3X^4X^5 \tag{1}$$

wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom.

The production method according to the present disclosure comprises obtaining a product comprising the fluoroethane from a fluoroethylene represented by the following formula (3) by a reaction in the presence of at least one catalyst:

$$CX^9F=CX^{10}X^{11} \tag{3}$$

wherein $X^9$, $X^{10}$, and $X^{11}$ are the same or different and each represents a hydrogen atom, a fluorine atom, or a chlorine atom.

Hereinafter, in the present specification, the method for producing a fluoroethane according to the present disclosure is referred to as "Production Method 1 according to the present disclosure."

In particular, in Production Method 1 according to the present disclosure, the reaction is performed in two or more reaction zones, each reaction zone comprises a catalyst, and the fluoroethylene is supplied to each reaction zone to perform the reaction.

In Production Method 1 according to the present disclosure, the desired product is a fluoroethane represented by formula (1) (hereinafter simply referred to as "fluoroethane"). In addition to the fluoroethane, by-products may also be produced in Production Method 1 according to the present disclosure. Thus, the product may be a mixed gas of the desired product and a by-product.

In Production Method 1 according to the present disclosure, examples of by-products include a fluoroethylene represented by the following formula (2):

$$CX^6F=CX^7X^8 \tag{2}$$

wherein $X^6$, $X^7$, and $X^8$ are the same or different and each represents a hydrogen atom, a fluorine atom, or a chlorine atom; and at least one of $X^6$, $X^7$, and $X^8$ represents a hydrogen atom.

Production Method 1 according to the present disclosure enables the desired fluoroethane to be obtained with high selectivity. Moreover, in Production Method 1 according to the present disclosure, blockage and corrosion of the reactor are less likely to occur during the hydrogenation reaction.

Product

In Production Method 1 according to the present disclosure, the fluoroethane contained in the product is the main product and the desired product in Production Method 1 according to the present disclosure. The term "main product" as used herein means a component that is present in an amount of 50 mol % or more in the product.

The fluoroethane is not limited, as long as it is a compound represented by formula (1). In formula (1), at least one of $X^1$, $X^2$, $X^3$, $X^4$, and $X^5$ represents a hydrogen atom; for example, $X^5$ may be a hydrogen atom. It is preferable that at least one of $X^1$, $X^2$, $X^3$, $X^4$, and $X^5$ is a fluorine atom.

Specific examples of the fluoroethane include at least one member selected from the group consisting of 1-chloro-1-fluoroethane (HCFC-151), fluoroethane (HFC-161), 1,2-dichloro-1,2-difluoroethane (HCFC-132), 2-chloro-1,1-difluoroethane (HCFC-142), 1-chloro-1,2-difluoroethane (HCFC-142a), 1,2-difluoroethane (HFC-152), 1,1-difluoroethane (HFC-152a), 2-chloro-1,1,2-trifluoroethane (HCFC-133), 1-chloro-1,1,2-trifluoroethane (HCFC-133b), 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a).

In Production Method 1 according to the present disclosure, one or more of the fluoroethanes described above are produced. That is, in Production Method 1, the product comprises one or more of the fluoroethanes described above. It is more preferable that the fluoroethane, which is the main product in Production Method 1 according to the present disclosure, comprises at least 1,1,2-trifluoroethane (HFC-143); and it is particularly preferable that 1,1,2-trifluoroethane (HFC-143) is the main product. When 1,1,2-trifluoroethane (HFC-143) is the main product, for example, HCFC-133 and HCFC-133b may also be produced simultaneously.

Among by-products that may be produced in Production Method 1 according to the present disclosure, the fluoroethylene represented by formula (2) preferably comprises at least one member selected from the group consisting of trifluoroethylene (HFO-1123), 1,2-difluoroethylene (HFO-1132), 1,1-difluoroethylene (HFO-1132a), fluoroethylene (HFO-1141), 1-chloro-2-fluoroethylene, and 1,2-dichlorofluoroethylene (HCFO-1121). The fluoroethylene represented by formula (2) particularly preferably comprises trifluoroethylene (HFO-1123) among these. In Production Method 1 according to the present disclosure, one or more by-products are produced.

In Production Method 1, the product preferably comprises 1,1,2-trifluoroethane in an amount of 60 mol % or more, more preferably 70 mol % or more, and particularly preferably 80 mol % or more, based on the total amount of the product.

In Production Method 1, the product preferably comprises trifluoroethylene in an amount of 40 mol % or less, more preferably 30 mol % or less, and particularly preferably 20 mol % or less, based on the total amount of the product.

In Production Method 1, the product may be purified to increase the purity of the desired compound, or the product obtained without purification may be used as the desired compound. Moreover, when the product contains an unreacted starting material, the starting material can be separated by an appropriate method and used again as a starting material for the reaction. Specifically, in Production Method 1, the crude product can be used for the recycling of a starting material.

Starting Material

In Production Method 1 according to the present disclosure, the fluoroethylene represented by formula (3) is a starting material for obtaining the desired product and a starting material for the reaction performed in Production Method 1 according to the present disclosure. The fluoroethylene represented by formula (3) can be suitably selected according to the structural formula of the desired fluoroethane.

For example, the fluoroethylene represented by formula (3) is preferably at least one member selected from the group consisting of fluoroethylene (HFO-1141), 1,2-dichloro-1,2-difluoroethylene (CFO-1112), 1,1-difluoroethylene (HFO-1132a), 1,2-difluoroethylene (HFO-1132), chlorotrifluoroethylene (CTFE, CFO-1113), trifluoroethylene (HFO-1123), 2-chloro-1,1-difluoroethylene (HCFO-1122), 1-chloro-1,2-difluoroethylene (HCFO-1122a), and tetrafluoroethylene (FO-1114). Among these, the fluoroethylene more preferably comprises at least one member selected from the group consisting of chlorotrifluoroethylene (CTFE, CFO-1113) and tetrafluoroethylene (FO-1114); the fluoroethylene particularly preferably comprises chlorotrifluoroethylene (CTFE, CFO-1113).

The fluoroethylenes represented by formula (3) may be used singly, or in a combination of two or more. When a single fluoroethylene represented by formula (3) is used, the fluoroethylene may contain, for example, impurities that may be inevitably present; or other components.

Reaction and Reaction Zone

In Production Method 1 according to the present disclosure, a fluoroethylene represented by formula (3) is subjected to a reaction in the presence of at least one catalyst. In Production Method 1 according to the present disclosure, the reaction is, for example, a hydrogenation reaction. In Production Method 1 according to the present disclosure, the reaction may also include one or both of a dehydrochlorination reaction and a hydrogen chloride addition reaction, in addition to the hydrogenation reaction.

In Production Method 1 according to the present disclosure, the reaction is performed by reacting the fluoroethylene represented by formula (3) with hydrogen gas in the presence of at least one catalyst in one or more reactors. This reaction is generally performed in a gas phase. In Production Method 1 according to the present disclosure, the reaction can be performed either continuously, or batch-wise.

In particular, in Production Method 1 according to the present disclosure, the reaction is performed in two or more reaction zones. The term "reaction zone" as used herein refers to a region in which a catalyst for reaction is provided, and in which a reaction (i.e., a hydrogenation reaction) is performed. In Production Method 1 according to the present disclosure, when the fluoroethylene represented by formula (3) and hydrogen are introduced into reactor(s) having the reaction zones to bring these gases into contact with the catalyst provided in each reaction zone, a hydrogenation reaction proceeds; and, further, a dehydrochlorination reaction and hydrogen chloride addition reaction accompanying the hydrogenation reaction can also proceed. The details of the catalyst are described later.

In Production Method 1 according to the present disclosure, at least two or more reaction zones are provided.

Two or more reaction zones may be provided, for example, in one reactor for performing the reaction. Alternatively, in Production Method 1 according to the present disclosure, when a hydrogenation reaction is performed using a reaction apparatus in which two or more reactors are connected in series, a reaction zone may be provided in each reactor constituting the reaction apparatus. From the viewpoint that the selectivity of the desired fluoroethane is easily increased, and that blockage and corrosion of a reactor are less likely to occur, it is preferable to use a reaction apparatus in which two or more reactors are connected in series, and to provide one reaction zone in each reactor.

Specifically, in Production Method 1 according to the present disclosure, it is more preferable that the reaction is performed in a reaction apparatus in which two or more reactors are connected in series, and that each reactor comprises a reaction zone. In other words, in a more preferable embodiment of Production Method 1 according to the present disclosure, the reaction is performed in a reaction apparatus in which two or more reactors are connected in series, and each reactor is filled with a catalyst. Hereinafter, the reaction apparatus used in this embodiment is referred to as "reaction apparatus A."

Reaction apparatus A comprises two or more catalyst-filled reactors that are connected in series. The method for connecting two or more reactors in series is not limited. For example, the reactors may be connected side by side so as to be parallel to each other (for example, see FIG. 1 described later).

In reaction apparatus A, adjacent reactors among the plurality of reactors can be connected to each other via, for example, a pipe. The number of reactors connected in series is not limited, as long as it is two or more; and can be suitably set depending on the capacity of the reactors, the amount of fluoroethane to be produced, and the like. The number of reactors is preferably five or less, from the viewpoint that a fluoroethane can be obtained with the desired selectivity without reaction apparatus A becoming overly large.

In reaction apparatus A, various pieces of equipment, such as a heat exchanger and a cooler, may also be provided at the connection portions of the reactors. Moreover, a device for removing hydrochloric acid or the like that causes by-products may also be disposed between adjacent reactors. Examples of the device include distillation equipment, adsorption equipment, and the like.

In reaction apparatus A, each reactor is filled with a catalyst. Thereby, a reaction zone is formed in each reactor. The method for filling a reactor with a catalyst is not limited; and may be, for example, a method that is the same as or similar to that in known hydrogenation reactions.

The method for performing a hydrogenation reaction using reaction apparatus A is not limited. For example, when the gaseous fluoroethylene and hydrogen are introduced into a reactor at one end of reaction apparatus A (hereinafter referred to as "first reactor") from the outside and allowed to pass through a catalyst (reaction zone) filled in the first reactor, a hydrogenation reaction of the fluoroethylene proceeds; and further, a dehydrochlorination reaction and hydrogen chloride addition reaction accompanying the hydrogenation reaction can also proceed. In the first reactor, the mixed gas obtained after the starting materials pass through the catalyst contains unreacted fluoroethylene and hydrogen, the fluoroethane produced, and one or more by-products. The mixed gas flows into a reactor connected in series to the first reactor (hereinafter referred to as "second reactor").

The mixed gas flowing into the second reactor further passes through a catalyst filled in the reactor. Fresh starting material fluoroethylene is introduced into the second reactor from the outside. In this case, fresh fluoroethylene may be introduced from an inlet that is different from the inlet of the second reactor from which the mixed gas flowing in from the first reactor is introduced. If necessary, additional hydrogen gas can be introduced into the second reactor from the outside, together with fresh fluoroethylene.

As in the first reactor, a mixed gas obtained after the above materials pass through the catalyst (reaction zone) is obtained in the second reactor. The mixed gas may contain unreacted fluoroethylene and hydrogen, and by-products, in addition to the fluoroethane produced in the first reactor and the second reactor. When there is a reactor that is further connected in series to the second reactor (hereinafter referred to as "third reactor"), this mixed gas flows into the third reactor.

As described above, in Production Method 1 according to the present disclosure, when there are three or more reactors, the reaction is performed sequentially in the reaction zone in each of the third and subsequent reactors of reaction apparatus A, in the same manner as in the first reactor and the second reactor. For example, when reaction apparatus A comprises n reactors (n is an integer of two or more), the reaction is performed sequentially up to the nth reactor, counting from the first reactor. Specifically, the mixed gas flowing out of the first reactor passes through the second reactor, the third reactor . . . and the n−1th reactor sequentially; and finally reaches the nth reactor. In each reactor, fresh fluoroethylene may be introduced from the outside in the same manner as in the second reactor; and further, hydrogen gas may also be introduced from the outside as necessary.

By the above procedure, the reaction is performed in each reactor in reaction apparatus A; and finally, the mixed gas can be collected from the nth reactor to obtain the desired fluoroethane.

In each reactor, the flow speed (also called the "flow rate") of fluoroethylene introduced from the outside is not limited; and may be, for example, 60 mL/h to 500 kL/h. In each reactor, the flow speed of hydrogen gas introduced from the outside is not limited; and may be, for example, 60 mL/h to 1000 kL/h. The flow speed of fluoroethylene may vary from reactor to reactor. The flow speed of hydrogen gas may also vary from reactor to reactor.

When reaction apparatus A is used in Production Method 1 according to the present disclosure, the amount of hydrogen gas used in the first reactor is not limited; and, for example, may be the same as or similar to that in known hydrogenation reactions. For example, the amounts of the fluoroethylene represented by formula (3) and hydrogen gas may be adjusted such that the amount of hydrogen gas is 1 to 25 moles, per mole of the fluoroethylene represented by formula (3). The amount of hydrogen gas is preferably 1 to 15 moles, and more preferably 1 to 5 moles, per mole of the fluoroethylene represented by formula (3).

In Production Method 1 according to the present disclosure, the reaction temperature is not limited; and may be, for example, 50 to 400° C., preferably 100 to 390° C., and more preferably 150 to 380° C. The temperature of the reaction of the fluoroethylene may vary from reactor to reactor. For example, the reaction temperature may increase toward the downstream side of the hydrogenation reaction (i.e., from the first reactor toward the nth reactor). In this case, the amount of intermediate product and by-product of the reaction described later mixed in the ultimately obtained fluoroethane can be significantly suppressed. In the first reactor, in which the main reaction is an exothermic reaction, the temperature becomes high naturally; thus, heating is necessary to promote the reaction. When the temperature rises sharply due to exothermic heat, the reactor may be cooled as necessary. On the other hand, since an endothermic reaction may occur in the nth reactor, the reactor may be heated as necessary.

In Production Method 1 according to the present disclosure, the hydrogenation reaction may be performed under reduced pressure, atmospheric pressure, or increased pressure. For example, in Production Method 1 according to the present disclosure, the pressure during the reaction is preferably 2 MPaG or less, more preferably 1 MPaG or less, and particularly preferably 0.3 MPaG or less, from the viewpoint of reactivity. The G in "MPaG" means gauge pressure, and indicates the value displayed on a pressure gauge relative to atmospheric pressure (i.e., atmospheric pressure=0 MPaG). The pressure during the reaction may be constant or different between the first reactor to the nth reactor. Moreover, the reaction may also be performed either in the presence of an inert gas, or in the presence of air.

In Production Method 1 according to the present disclosure, the reaction time is not limited. For example, the contact time represented by W/Fo, i.e., the ratio of the catalyst amount in a reactor W (g) to the total flow rate of the fluoroethylene and hydrogen gas introduced into the reactor Fo, may be 1 to 100 g·sec/cc.

In Production Method 1 according to the present disclosure, for example, when chlorotrifluoroethylene is used as a starting material, the intermediate product of the hydrogenation reaction is trifluoroethylene. In Production Method 1 according to the present disclosure, for example, when chlorotrifluoroethylene is used as a starting material, the by-product of the hydrogenation reaction is one or more members selected from 1-chloro-1-fluoroethane (HCFC-151), fluoroethane (HFC-161), chloro-1,2-difluoroethane (HCFC-142), 1,2-difluoroethane (HFC-152), 1,1-difluoroethane (HFC-152a), 2-chloro-1,1,2-trifluoroethane (HCFC-133), 1-chloro-1,1,2-trifluoroethane (HCFC-133b), 1,1,1-trifluoroethane (HFC-143a), trifluoroethylene (HFO-1123), 1,1-difluoroethylene (HFO-1132a), 1,2-difluoroethylene (HFO-1132), ethylene, chloroethane, and the like.

In Production Method 1 according to the present disclosure, the reactor(s) may be, for example tubular flow reactors. For example, the flow reactor may be an adiabatic reactor, a multitubular reactor in which a heating medium is used to slowly cool the reactor, or the like. The reactor(s) are preferably formed of a material that is resistant to corrosive action, such as stainless steel (SUS). In particular, the reactor(s) are preferably formed of Hastelloy, Inconel, Monel, or the like.

The reactor(s) may also be provided with a jacket for adjusting the temperature inside the reactor(s). For example, a heating medium or the like may be circulated in the jacket. This makes it possible to adjust the temperature of the gases (e.g., the starting materials fluoroethylene and hydrogen) in the reactor(s).

Since two or more reaction zones are provided in Production Method 1 according to the present disclosure, the starting material fluoroethylene can be dispersively introduced into the individual reaction zones, compared with the case in which the hydrogenation reaction is performed in only one reaction zone. This allows the concentration of the fluoroethylene in the reaction site to be reduced; accordingly, the fluoroethylene polymerization reaction, which occurs as a side reaction in conventional methods, is more easily suppressed. As a result, the excessive temperature rise in a reactor and the amount of polymer of the fluoroethylene produced are notably suppressed. Moreover, the amount of intermediate product and by-product of the reaction mixed in the ultimately obtained fluoroethane can be significantly suppressed. Further, a mixture of the fluoroethylene and the fluoroethane can also be obtained while ensuring high conversion and high selectivity by adjusting the reaction conditions.

Production Method 1 according to the present disclosure may also comprise, if necessary, other steps in addition to the step of obtaining the fluoroethane.

Catalyst

The type of catalyst used in the reaction in Production Method 1 according to the present disclosure is not limited. For example, a wide range of known catalysts used in a hydrogenation reaction can be used.

Examples of the noble metal include palladium (Pd), platinum (Pt), ruthenium (Ru), rhodium (Rh), nickel (Ni), cobalt (Co), and the like. The noble metal is preferably one or more members selected from the group consisting of palladium, platinum, and nickel. The noble metal particularly preferably comprises palladium.

Examples of the carrier in the catalyst used in Production Method 1 according to the present disclosure include activated carbon, porous aluminosilicate typified by zeolite, aluminum oxide, silicon oxide, titanium oxide, zirconium oxide, zinc oxide, aluminum fluoride, and the like. The carrier may be foamed of only one material, or may be formed of two or more materials.

The method for preparing the catalyst is not limited, and a wide range of know methods can be used. An example of the method for preparing a catalyst comprising a noble metal supported on a carrier is as below. That is, a carrier is immersed in a solution containing a noble metal to impregnate the carrier with the solution, if necessary, followed by neutralization, calcination, and the like, thereby obtaining the catalyst. In this case, the amount of noble metal supported on the carrier can be controlled by adjusting the concentration of the solution, the impregnation time, and the like.

In Production Method 1 according to the present disclosure, the amount of catalyst used is not limited; and may be, for example, the same as or similar to that in known hydrogenation reactions. For example, the amount of catalyst used can be suitably set depending on the size of a reaction tube or reactor, the amount of starting material used, the amount of fluoroethane to be produced, and the like.

In Production Method 1 according to the present disclosure, the catalyst is formed by supporting a noble metal on a carrier. It is preferable that the reaction zones are filled with a catalyst having a noble metal concentration of C1 mass % based on the entire catalyst, and a catalyst having a noble metal concentration of C2 mass % based on the entire catalyst to form an upstream portion and a downstream portion, respectively; and that C1<C2. In this case, the reaction is performed by bringing the fluoroethylene represented by formula (3) and hydrogen gas into contact with the upstream portion and the downstream portion in this order. In the present disclosure, in a reactor, the inlet side into which the starting materials are introduced is referred to as the upstream portion, and the outlet side is referred to as the downstream portion.

In Production Method 1 according to the present disclosure, when a reaction apparatus in which two or more reactors are connected in series as in reaction apparatus A described above is used, it is preferable that in adjacent reactors, the concentration of the noble metal in the catalyst contained in each reactor is higher on the downstream side of the flow of the fluoroethylene than on the upstream side.

In particular, in Production Method 1 according to the present disclosure, when a reaction apparatus in which two or more reactors are connected in series as in reaction apparatus A described above is used, it is more preferable that the concentration of the noble metal in the catalyst contained in each reactor becomes higher toward the downstream side of the flow of the fluoroethylene. In these cases, as described later, the excessive temperature rise in the reactors and the amount of polymer of the fluoroethylene produced are notably suppressed. Moreover, the amount of intermediate product and by-product of the hydrogenation reaction mixed in the ultimately obtained fluoroethane can be significantly suppressed.

In Production Method 1 according to the present disclosure, the positions of the upstream portion and the downstream portion provided in a reactor are not limited. For example, the upstream portion and the downstream portion may be provided so as to be adjacent to each other, or the upstream portion and the downstream portion may be provided with a gap between them. Further, a catalyst may be placed between the upstream portion and the downstream portion to form a midstream portion. The midstream portion may be formed of only one layer, or two or more layers. When the noble metal concentration of the catalyst forming the midstream portion is expressed as $C^M$ mass %, the noble metal concentration may be set such that $C1<C^M<C2$.

The thicknesses of the upstream portion and the downstream portion are also not limited; and can be suitably selected depending on, for example, the size of a reactor and the gas flow rate. The thicknesses of the upstream portion and the downstream portion refer to the lengths in the direction in which the starting materials flow.

In the upstream portion, the amount of noble metal supported, i.e., C1 (mass %), based on the total mass of the catalyst may be adjusted, for example, to 0.01 to 10 mass %, and preferably 0.1 to 3 mass %.

In the downstream portion, the amount of noble metal supported, i.e., C2 (mass %), based on the total mass of the catalyst may be adjusted, for example, to 1 to 15 mass %, and preferably 1 to 5 mass %.

In Production Method 1 according to the present disclosure, the reaction temperature in the upstream portion (the ambient temperature when the starting materials come into contact with the upstream portion) may be 100 to 500° C., and preferably 200 to 400° C. In Production Method 1 according to the present disclosure, the reaction temperature in the downstream portion (the ambient temperature when the starting materials come into contact with the downstream portion) can be suitably adjusted depending on the type of desired product. The reaction temperature in the downstream portion may be, for example, 100 to 400° C., and preferably 150 to 300° C. The reaction temperature in the upstream portion is preferably 400° C. or less, from the viewpoint of preventing, for example, polymerization of the fluoroethylene, which is a starting material, explosion, and catalyst deterioration; and the temperature can be adjusted by cooling as necessary.

In Production Method 1 according to the present disclosure, when reaction apparatus A is used, the upstream portion and the downstream portion may be formed in all of the reactors.

In Production Method 1 according to the present disclosure, when the upstream portion and the downstream portion are formed in reaction zones, the fluoroethylene represented by formula (3) and hydrogen gas pass through the catalyst having lower activity first, and then through the catalyst in the downstream portion that has activity higher than that in the upstream portion. This makes it easier to suppress a fluoroethylene polymerization reaction, which occurs as a side reaction in conventional methods, resulting in significant suppression of an excessive temperature rise in a reactor and of the amount of polymer of the fluoroethylene produced. Moreover, the amount of intermediate product and by-product of the hydrogenation reaction mixed in the ultimately obtained fluoroethane can be notably suppressed. Thus, in Production Method 1 according to the present disclosure, the selectivity and yield of the product can be controlled by the catalyst in the downstream portion and the reaction temperature.

2. Method for Producing Fluoroolefin

The method for producing a fluoroolefin according to the present disclosure comprises obtaining a fluoroolefin by a dehydrofluorination reaction of a fluoroethane obtained in the method for producing a fluoroethane described above (Production Method 1). Hereinafter, this step is referred to as "the dehydrofluorination step," and the method for producing a fluoroolefin according to the present disclosure is referred to as "Production Method 2 according to the present disclosure."

In Production Method 2 according to the present disclosure, for example, a fluoroolefin represented by the following formula (4) can be obtained:

$$CX^{11}X^{21}=CX^{31}X^{41} \qquad (4)$$

wherein $X^{11}$, $X^{21}$, $X^{31}$, and $X^{41}$ are the same or different and each represents a hydrogen atom, a fluorine atom, or a chlorine atom; at least one of $X^{11}$, $X^{21}$, $X^{31}$, and $X^{41}$ represents a hydrogen atom; and at least one of $X^{11}$, $X^{21}$, $X^{31}$, and $X^{41}$ represents a fluorine atom.

In the dehydrofluorination step, the method for the dehydrofluorination reaction is not limited. For example, the dehydrofluorination reaction may be performed under conditions that are the same as or similar to those of known dehydrofluorination reactions. For example, the dehydrofluorination reaction may be performed in a gas phase, in the presence of a catalyst for dehydrofluorination.

In Production Method 2 according to the present disclosure, the dehydrofluorination reaction when 1,1,2-trifluoroethane (HFC-143) is used as a fluoroethane is performed according to the following reaction scheme.

$$CF_2HCFH_2 \rightarrow CHF=CHF+HF$$

The catalyst for dehydrofluorination is not limited, and a wide range of known catalysts can be used. Examples include chromium oxide, fluorinated chromium oxide, aluminum oxide, fluorinated aluminum oxide, and the like.

The catalyst for dehydrofluorination is preferably supported on a carrier. Examples of carriers include carbon, alumina ($Al_2O_3$), zirconia ($ZrO_2$), silica ($SiO_2$), titania ($TiO_2$), and the like. As carbon, activated carbon, amorphous carbon, graphite, diamond, or the like can be used.

In Production Method 2 according to the present disclosure, the dehydrofluorination reaction may also be performed in the presence of an oxidizing agent. Examples of oxidizing agents include oxygen, chlorine, bromine, iodine, and the like. Oxygen is particularly preferable. The concentration of the oxidizing agent is not limited; and may be, for example, the same as or similar to that in known dehydrofluorination reactions.

The reaction temperature in the dehydrofluorination reaction is also not limited; and may be the same as or similar to that in known dehydrofluorination reactions. For example, the reaction temperature in the dehydrofluorination reaction may be, for example, 300° C. or more, preferably 320° C. or more, more preferably 340° C. or more, and particularly preferably 350° C. or more. The reaction temperature in the dehydrofluorination reaction may also be 600° C. or less, preferably 550° C. or less, more preferably 500° C. or less, and particularly preferably 450° C. or less.

The reaction time of the dehydrofluorination reaction and the pressure during the reaction are also not limited, and a wide range of known conditions can be adopted. The dehydrofluorination reaction may also be performed either in the presence of an inert gas, or in the presence of air. The dehydrofluorination reaction may be performed either continuously, or batch-wise.

Production Method 2 according to the present disclosure may also comprise, if necessary, other steps in addition to the dehydrofluorination step. Also in Production Method 2, the starting material can be separated from the crude product obtained in Production Method 2, and recycled.

For example, a compound represented by formula (4) is obtained as the desired fluoroolefin by the dehydrofluorination step. In the dehydrofluorination step, one or more fluoroolefins are produced as the desired compounds.

The resulting fluoroolefin can depend on the fluoroethane used in the dehydrofluorination step. Examples of fluoroolefins include 1,2-difluoroethylene (HFO-1132), 1,1-difluoroethylene (HFO-1132a), trifluoroethylene (HFO-1123), and the like.

In Production Method 2 according to the present disclosure, when HFC-143 is used as a fluoroethane, the resulting fluoroolefin is HFO-1132. In Production Method 2 according to the present disclosure, when HFC-143a is used as a fluoroethane, the resulting fluoroolefin is HFO-1132a. In Production Method 2 according to the present disclosure, when HFC-134 is used as a fluoroethane, the resulting fluoroolefin is HFO-1123. HFO-1132 can include trans-1,2-difluoroethylene [(E)-HFO-1132] and cis-1,2-difluoroethylene [(Z)-HFO-1132].

When a fluoroolefin is obtained by Production Method 2 according to the present disclosure, Production Method 1 according to the present disclosure and Production Method 2 according to the present disclosure may be performed consecutively, or may be performed independently.

For example, the present disclosure includes the inventions described in the following items.

Item 1

A method for producing a fluoroethane represented by the following formula (1):

$$CX^1X^2FCX^3X^4X^5 \quad (1),$$

wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom, the method comprising obtaining a product comprising the fluoroethane from a fluoroethylene represented by the following formula (3) by a reaction in the presence of at least one catalyst:

$$CX^9F=CX^{10}X^{11} \quad (3),$$

wherein $X^9$, $X^{10}$, and $X^{11}$ are the same or different and each represents a hydrogen atom, a fluorine atom, or a chlorine atom, wherein the reaction is performed in two or more reaction zones, and each reaction zone comprises a catalyst; and the fluoroethylene is supplied to each reaction zone to perform the reaction.

Item 2

The method for producing a fluoroethane according to Item 1, wherein the reaction is performed in a reaction apparatus in which two or more reactors are connected in series, and each reactor comprises a reaction zone.

Item 3

The method for producing a fluoroethane according to Item 1 or 2, wherein the catalyst is formed by supporting a noble metal on a carrier; the reaction zones are filled with a catalyst having a noble metal concentration of C1 mass % based on the entire catalyst, and a catalyst having a noble metal concentration of C2 mass % based on the entire catalyst to form an upstream portion and a downstream portion, respectively, and C1<C2; and the reaction is performed by bringing the fluoroethylene represented by formula (3) and hydrogen gas into contact with the upstream portion and the downstream portion in this order.

Item 4

The method for producing a fluoroethane according to any one of Items 1 to 3, wherein the fluoroethylene comprises chlorotrifluoroethylene.

Item 5

The method for producing a fluoroethane according to any one of Items 1 to 4, wherein the fluoroethane comprises 1,1,2-trifluoroethane.

Item 6

The method according to Item 5, wherein the product comprises 1,1,2-trifluoroethane in an amount of 60 mol % or more based on the total amount of the product.

Item 7

The method according to any one of Items 1 to 6, wherein the product comprises trifluoroethylene in an amount of 40 mol % or less based on the total amount of the product.

Item 8

A method for producing a fluoroolefin, the method comprising obtaining a fluoroolefin by a dehydrofluorination reaction of a fluoroethane obtained by the method according to any one of Items 1 to 7.

EXAMPLES

The present disclosure is described in more detail below with reference to Examples. However, the present disclosure is not limited to the Examples.

Example 1

Figure 1:
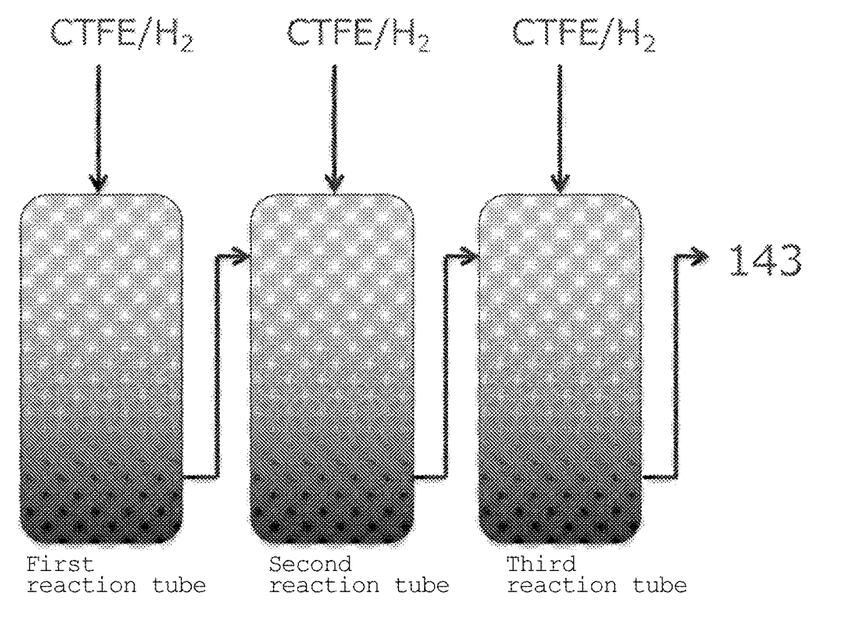
FIG. 1 is a schematic view showing the reaction apparatus used in the Examples.

A hydrogenation reaction was performed using a reaction apparatus schematically illustrated in FIG. 1. Specifically, a reaction apparatus in which three 5-L tubular reactors (which are referred to as "the first reactor," "the second reactor," and "the third reactor" from the upstream side of the starting material gas flow) were connected in series was prepared. A heat exchanger was provided between each of the reactors, and the reactors were connected. Each reactor was filled with 270 g of a catalyst to form individual reaction zones. The catalyst was famed by supporting palladium as a noble metal on activated carbon as a carrier. In all three of the reactors, the amount of palladium supported was 0.6 mass % based on the total mass of the catalyst in each reactor. Chlorotrifluoroethylene ("CTFE") and hydrogen were supplied at flow rates of 11.1 L/h and 108 L/h, respectively, from the starting material supply port of the first reactor in the reaction apparatus; and allowed to pass through the catalyst in the first reactor. In the first reactor, the temperature in the reaction zone (reaction temperature) was 350° C.

The resulting mixed gas was supplied from the first reactor to the second reactor, and fresh CTFE was also supplied to the second reactor at a flow rate of 11.1 L/h. They were allowed to pass through the catalyst in the second reactor. The mixed gas obtained after they passed through the catalyst in the second reactor was supplied to the third reactor, and fresh CTFE was also supplied to the third reactor at a flow rate of 11.1 L/h; they were allowed to pass through the catalyst in the third reactor. The temperature in the reaction zone (reaction temperature) in the second reactor and the temperature in the reaction zone (reaction temperature) in the third reactor were 350° C.

The mixed gas obtained after they passed through the catalyst in the third reactor was collected. The components in the collected mixed gas were analyzed by gas chromatography. In the above reaction, the contact time represented by W/Fo, i.e., the ratio of the catalyst amount in each reactor W (g) to the total flow rate of the fluoroethylene and hydrogen gas introduced into the reactor Fo, was 17 g·sec/cc.

Example 2

A hydrogenation reaction was performed using a reaction apparatus schematically illustrated in FIG. 1. Specifically, a reaction apparatus in which three 5-L tubular reactors (which are referred to as "the first reactor," "the second reactor," and "the third reactor" from the upstream side of the starting material gas flow) were connected in series was prepared. A heat exchanger was provided between each of the reactors, and the reactors were connected. Each reactor was filled with 270 g of a catalyst to form individual reaction zones. The catalyst was famed by supporting palladium as a noble metal on activated carbon as a carrier. The amount of palladium based on the total mass of the catalyst in each reactor was 0.1 mass % in the first reactor, 0.6 mass % in the second reactor, and 3 mass % in the third reactor. Chlorotrifluoroethylene ("CTFE") and hydrogen were supplied at flow rates of 11.1 L/h and 108 L/h, respectively, from the starting material supply port of the first reactor in the reaction apparatus; and allowed to pass through the catalyst in the first reactor. The temperature in the upstream portion was 320° C., and the temperature in the downstream portion was 230° C.

The resulting mixed gas was supplied from the first reactor to the second reactor, and fresh CTFE was also supplied to the second reactor at a flow rate of 11.1 L/h. They were allowed to pass through the catalyst in the second reactor. The mixed gas obtained after they passed through the catalyst in the second reactor was supplied to the third reactor, and fresh CTFE was also supplied to the third reactor at a flow rate of 11.1 L/h; they were allowed to pass through the catalyst in the third reactor.

The mixed gas obtained after they passed through the catalyst in the third reactor was collected. The components in the collected mixed gas were analyzed by gas chromatography. In the above reaction, the contact time represented by W/Fo, i.e., the ratio of the catalyst amount in each reactor W (g) to the total flow rate of the fluoroethylene and hydrogen gas introduced into the reactor Fo, was 17 g·sec/cc.

Comparative Example 1

One 25-L tubular reactor was prepared and filled with 810 g of a catalyst. The catalyst was formed using activated carbon as a carrier, and using palladium as a noble metal. The amount of palladium supported was 0.6 mass % based on the total mass of the catalyst. CTFE and hydrogen were supplied at flow rates of 33.3 L/h and 117 L/h, respectively, from the starting material supply port of the reactor; and allowed to pass through the catalyst. In the above reaction, the contact time represented by W/Fo, i.e., the ratio of the catalyst amount in the reactor W (g) to the total flow rate of the fluoroethylene and hydrogen gas introduced into the reactor Fo, was 19 g·sec/cc.

TABLE 1

| Detected component | Detected amount (mol %) | | |
| --- | --- | --- | --- |
| | Example 1 | Example 2 | Comparative Example 1 |
| HFC-143 | 97.2 | 99.0 | 86.1 |
| HFO-1123 | 0.2 | 0.1 | 4.6 |
| HCFC-133b | 1.1 | 0.6 | 2.4 |
| HCFC-133 | 0.4 | 0.3 | 1.4 |
| CTFE | 0.0 | 0.0 | 0.1 |
| Reaction gas temperature (maximum temperature) | 350° C. | 320° C. | 470° C. |

Table 1 shows the results of gas chromatography in the Examples and Comparative Example.

Table 1 shows that in the reaction performed by using Production Method 1 according to the present disclosure as in Example 1 and Example 2, the selectivity and yield of HFC-143, which is the desired product, were high; and the introduction of fluoroethylene (HFO-1123), which is an intermediate product, was small. Further, in Example 1, the introduction of other impurities was also suppressed. In contrast, in Comparative Example 1, the selectivity and yield of HFC-143 were low, and many intermediate products and impurities were observed. Further, in Comparative Example 1, blockage of the reactor occurred during the reaction due to polymer formation.

The above results reveal that Production Method 1 according to the present disclosure enables the desired fluoroethane to be produced with high selectivity, and is less likely to cause blockage and corrosion of a reaction tube.

The invention claimed is:

1. A method for producing a fluoroethane represented by the following formula (1):

$$CX^1X^2FCX^3X^4X^5 \qquad (1),$$

wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom, the method comprising obtaining a product comprising the fluoroethane from a fluoroethylene represented by the following formula (3) by a reaction in the presence of at least one catalyst:

$$CX^9F=CX^{10}X^{11} \qquad (3),$$

wherein $X^9$, $X^{10}$, and $X^{11}$ are the same or different and each represents a hydrogen atom, a fluorine atom, or a chlorine atom, wherein the reaction is performed in two or more reaction zones, and each reaction zone comprises a catalyst; and comprises chlorotrifluoroethylene is supplied to each reaction zone to perform the reaction.

2. The method for producing a fluoroethane according to claim 1, wherein the reaction is performed in a reaction apparatus in which two or more reactors are connected in series, and each reactor comprises a reaction zone.

3. The method for producing a fluoroethane according to claim 1, wherein the catalyst is formed by supporting a noble metal on a carrier; the reaction zones are filled with a catalyst having a noble metal concentration of C1 mass % based on the entire catalyst, and a catalyst having a noble metal concentration of C2 mass % based on the entire catalyst to form an upstream portion and a downstream portion, respectively, and C1<C2; and the reaction is performed by bringing the fluoroethylene represented by formula (3) and hydrogen gas into contact with the upstream portion and the downstream portion in this order.

4. The method for producing a fluoroethane according to claim 1, wherein the fluoroethane comprises 1,1,2-trifluoroethane.

5. The method according to claim 4, wherein the product comprises 1,1,2-trifluoroethane in an amount of 60 mol % or more based on the total amount of the product.

6. The method according to claim 1, wherein the product comprises trifluoroethylene in an amount of 40 mol % or less based on the total amount of the product.

7. A method for producing a fluoroolefin, the method comprising obtaining a fluoroolefin by a dehydrofluorination reaction of a fluoroethane obtained by the method according to claim 1.

* * * * *

UNITED STATES PATENT AND TRADEMARK OFFICE
CERTIFICATE OF CORRECTION

| | |
|---|---|
| PATENT NO. | : 11,377,406 B2 |
| APPLICATION NO. | : 17/350785 |
| DATED | : July 5, 2022 |
| INVENTOR(S) | : Tomoyuki Iwamoto et al. |

It is certified that error appears in the above-identified patent and that said Letters Patent is hereby corrected as shown below:

In the Claims

Column 14, Claim 1, Line 61 after atom, insert --wherein the fluoroethylene comprises chlorotrifluoroethylene,--

Column 14, Claim 1, Line 64, delete "comprises chlorotrifluoroethylene", and insert --the fluoroethylene-- before the phrase "is supplied to each reaction zone to perform the reaction."

Signed and Sealed this
Fourteenth Day of February, 2023

Katherine Kelly Vidal
*Director of the United States Patent and Trademark Office*